US012702356B2

(12) United States Patent
Huttunen

(10) Patent No.: US 12,702,356 B2
(45) Date of Patent: Aug. 11, 2026

(54) LOW COST RING DEVICE STRUCTURES

(71) Applicant: Oura Health Oy, Oulu (FI)

(72) Inventor: Heikki Juhani Huttunen, Oulu (FI)

(73) Assignee: Oura Health Oy, Oulu (FI)

( * ) Notice: Subject to any disclaimer, the term of this patent is extended or adjusted under 35 U.S.C. 154(b) by 332 days.

(21) Appl. No.: 18/354,407

(22) Filed: Jul. 18, 2023

(65) Prior Publication Data

US 2025/0025101 A1 Jan. 23, 2025

(51) Int. Cl.
*A61B 5/00* (2006.01)
*B29C 65/08* (2006.01)

(52) U.S. Cl.
CPC .......... *A61B 5/6802* (2013.01); *A61B 5/6826* (2013.01); *B29C 65/08* (2013.01); *A61B 2562/166* (2013.01); *A61B 2562/18* (2013.01); *B29C 2791/002* (2013.01)

(58) Field of Classification Search
CPC . A61B 5/6802; A61B 5/6826; A61B 5/02438; B29L 2031/7096
See application file for complete search history.

(56) References Cited

U.S. PATENT DOCUMENTS 10,918,289 B1 * 2/2021 Wasson ................ A61B 5/0022
12,052,816 B1 * 7/2024 Mars ........................ H05K 3/36
2021/0037932 A1 * 2/2021 Min ..................... A61B 5/0006
2024/0090783 A1 * 3/2024 Goo ...................... A61B 5/7455
2025/0017531 A1 * 1/2025 Barison ................ A61B 5/6826
2025/0221635 A1 * 7/2025 Sushita .............. A61B 5/02433

* cited by examiner

*Primary Examiner* — Kyle A Cook
(74) *Attorney, Agent, or Firm* — ArentFox Schiff LLP

(57) ABSTRACT

Methods, systems, and devices for forming a wearable ring device are described. A welding process may use ultrasonic welding to attach an outer lateral surface cover to the inner lateral surface cover, which may form an arcuate frame for the wearable ring device. The welding process may involve ultrasonic welding, which may melt one or more welding features (e.g., welding ribs) to attach the outer lateral surface cover to the inner lateral surface cover. In some examples, the welding features may be located on the outer lateral surface cover, the inner lateral surface cover, or both. To reduce negative effects on fragile components, such as a PCB of the wearable ring device, the fragile components may be disposed in a location away from the welding features. Further, in some cases, a material may be used to cover and shield the fragile components from ultrasonic waves during the welding procedure.

18 Claims, 6 Drawing Sheets

Welding Feature 310

300

Welding Feature 310

LOW COST RING DEVICE STRUCTURES

FIELD OF TECHNOLOGY

The following relates to wearable devices and data processing, including low cost ring device structures.

BACKGROUND

Some wearable devices may be configured to collect data from users including heart rate, motion data, temperature data, photoplethysmogram (PPG) data, and the like. Some wearable devices may be configured with circuitry, such as a printed circuit board (PCB) that may be configured to operate (e.g., control, manage) one or more sensors of the wearable devices in order to collect the physiological data from the users. Manufacturing the wearable devices may be complex, and it may be desirable to reduce costs associated with manufacturing the wearable devices.

DETAILED DESCRIPTION

A manufacturing operation utilizing plastic materials, such as polycarbonate for manufacturing wearable devices may lower material expenses and expedite manufacturing of wearable devices compared to the use of metal materials. However, the manufacturing operation of attaching or welding different parts of a wearable device, such as inner and outer covers, may be challenging and potentially result in damage to sensitive components, including crystalline elements within a printed circuit board (PCB) of the wearable device. Therefore, when employing techniques for welding plastic components to manufacture (e.g., create, build, engineer) a wearable device (e.g., a wearable ring device or any other form of wearable), it is crucial to consider the vulnerabilities of the various components.

Various aspects of the present disclosure relate to a welding operation (e.g., process, procedure) utilizing ultrasonic welding to attach (e.g., connect, couple) an outer lateral surface cover to an inner lateral surface cover, thus forming a wearable device. The outer lateral surface cover and the inner lateral surface cover, including the welding features, may be formed using an injection molding operation (e.g., process, procedure, technique). The welding operation may involve the use of ultrasonic energy to melt one or more welding features (e.g., welding ribs) in order to attach the outer lateral surface cover to the inner lateral surface cover. These welding features may be present (e.g., positioned, located) on the outer lateral surface cover, the inner lateral surface cover, or both. To mitigate any potential adverse effects on fragile components, such as a PCB of the wearable device, these components may be positioned away from the welding features (e.g., disposed in a location away from the welding features). A protective material may also be used to cover and shield the fragile components from ultrasonic waves during the welding operation. Additionally, transparent lenses, serving as data-collecting sensors for the wearable device, may be added to the inner lateral surface cover (as molded plastic) and integrated into the lateral surface cover.

Aspects of the disclosure are initially described in the context of systems supporting physiological data collection from users via wearable devices. Aspects of the disclosure are additionally illustrated with respect to diagrams and welding assembly diagrams. Aspects of the disclosure are further illustrated by and described with reference to apparatus diagrams, system diagrams, and flowcharts that relate to low cost ring device structures.

Figure 1:
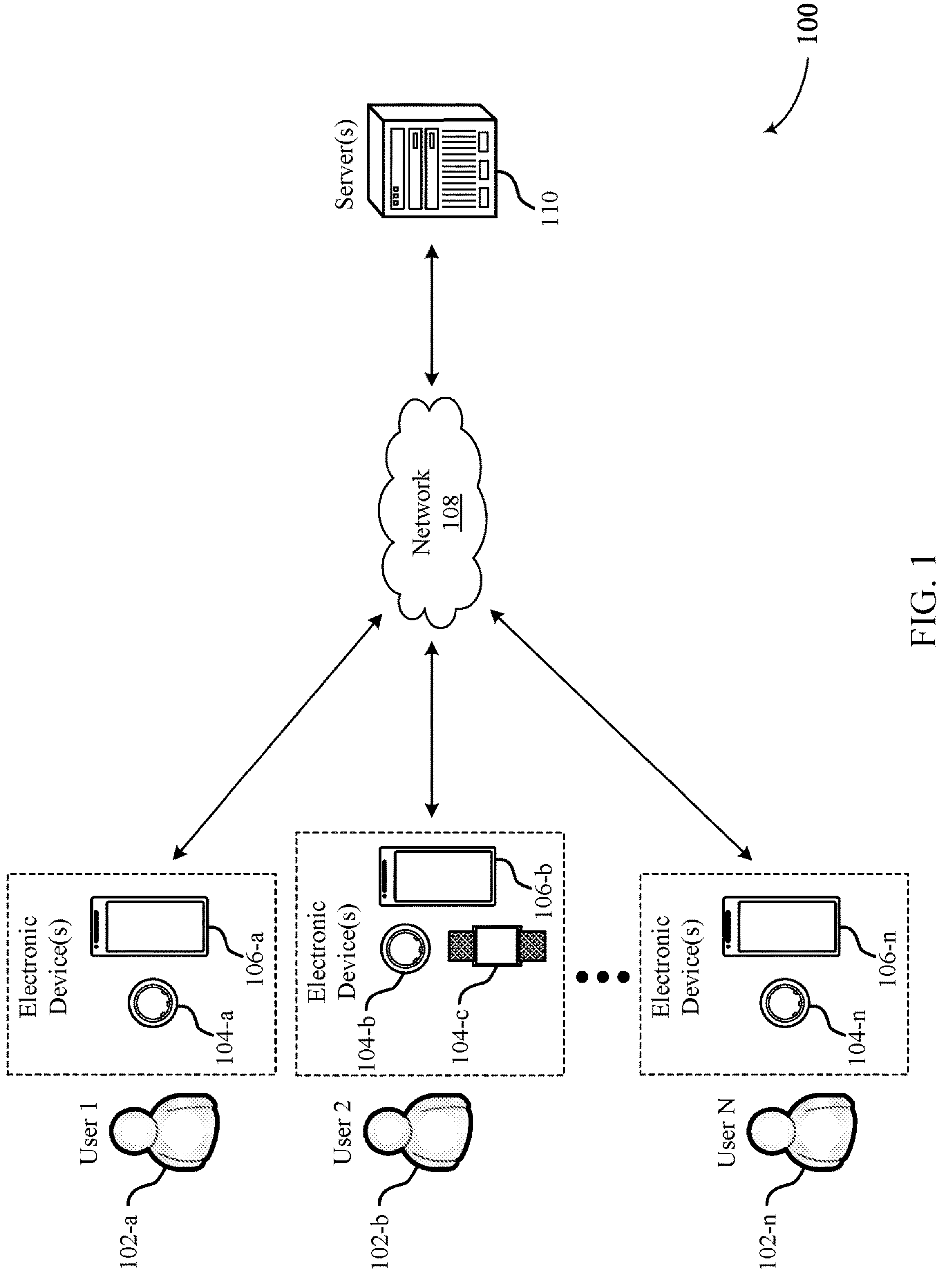
FIG. 1 illustrates an example of a system that supports low cost ring device structures in accordance with aspects of the present disclosure.

FIG. 1 illustrates an example of a system 100 that supports low cost ring device structures in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled with one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled with the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Further, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled with one or more servers 110 via wired or wireless communication protocols. For example, as shown in FIG. 1, the electronic devices (e.g., user devices 106) may be communicatively coupled with one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled with the user device 106-*a*, where the user device 106-*a* is communicatively coupled with the servers 110 via the network 108. In additional or alternative cases, wearable devices 104 (e.g., rings 104, watches 104) may be directly communicatively coupled with the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight." or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules: 4) weekly rhythms, or other artificial time periodicities exogenously imposed (e.g., in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for low cost ring device structures as described herein. For example, a welding process may use ultrasonic welding to attach an outer lateral surface cover to the inner lateral surface cover in forming a wearable device 104. The welding process may involve ultrasonic welding, which may melt one or more welding features (e.g., welding ribs) to attach the outer lateral surface cover to the inner lateral surface cover. In some examples, the welding features may be located on the outer lateral surface cover, the inner lateral surface cover, or both.

To reduce negative effects on fragile components, such as a PCB of the wearable ring device (or other form factor wearable device), the fragile components may be disposed in a location away from the welding features. Further, in some cases, a material may be used to cover and shield the fragile components from ultrasonic waves during the welding procedure. In some examples, the outer lateral surface cover and the inner lateral surface cover, including the welding features, may be formed using injection molding techniques. In some instances, one or more ultrasonic welding heads may be designed in a circular shape, allowing the entire wearable device to be welded concurrently during the welding procedure. In some examples, transparent lenses for the wearable device 104 may be added to the inner lateral surface cover (e.g., as molded plastic) and integrated into the inner lateral surface cover, which may allow a wearable device 104 to collect physiological data from a user 102 via one or more sensors, as described herein.

Accordingly, by incorporating these techniques, wearable devices 104 may be formed from plastic materials using a welding procedure while protecting fragile components of the wearable devices 104, thereby reducing material costs and speeding up production relative to using metal materials.

It should be appreciated by a person skilled in the art that one or more aspects of the disclosure may be implemented in a system 100 to additionally or alternatively solve other problems than those described herein. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
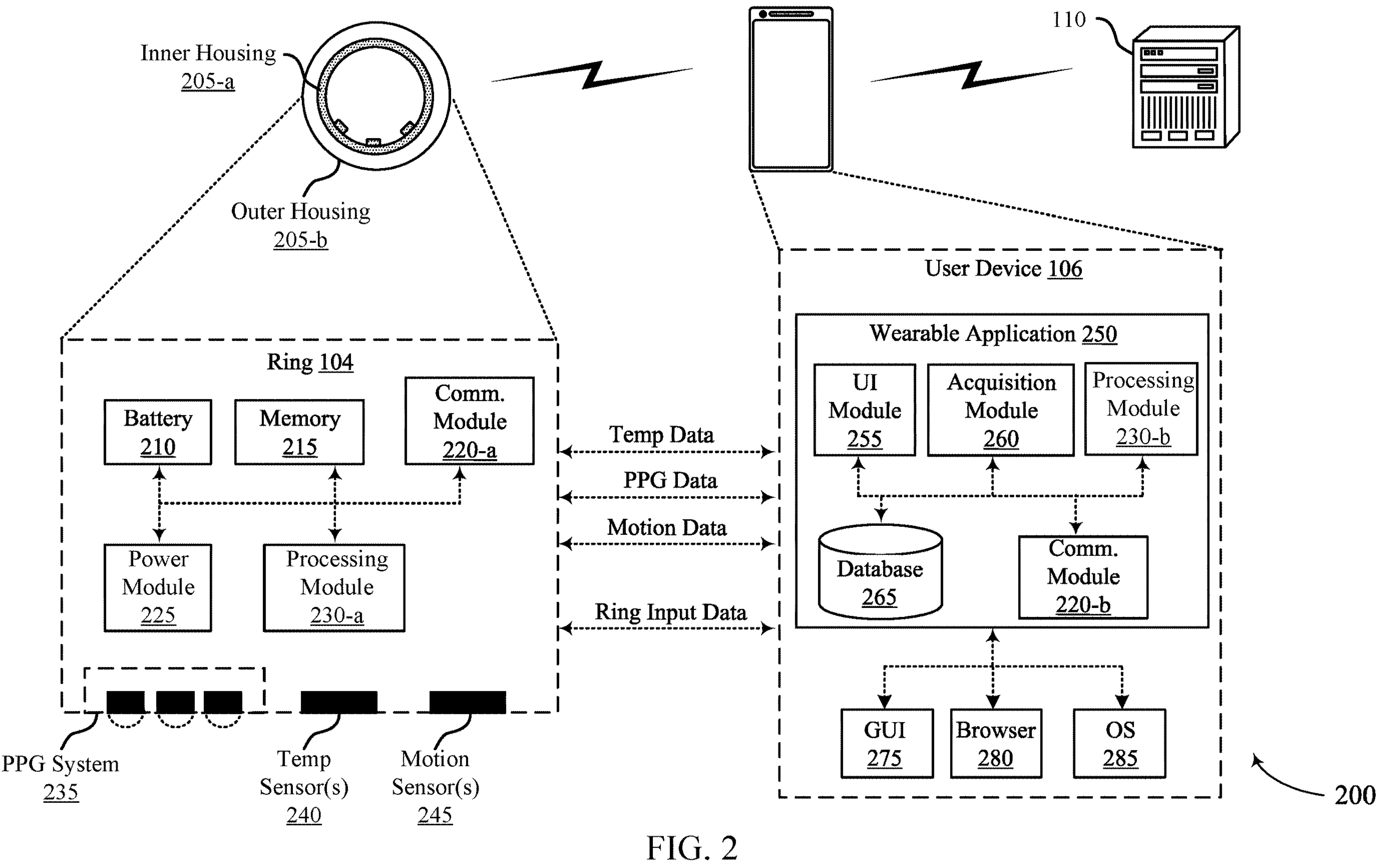
FIG. 2 illustrates an example of a system that supports low cost ring device structures in accordance with aspects of the present disclosure.

FIG. 2 illustrates an example of a system 200 that supports low cost ring device structures in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled with one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled with the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the quantity of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The quantity and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a quantity of acceleration peaks within one or more periods of time (e.g., one or more 30 second to 1 minute periods). Intensity values may indicate a quantity of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the quantity of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the quantity of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score)

may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for a ring device structure as described herein. For example, the inner housing 205-*a* and the outer housing 205-*b* may be formed using injection molding techniques, and the inner housing 205-*a*, the outer housing 205-*b*, or both, may include one or more welding features (e.g., welding ribs). A welding operation (e.g., welding process, welding procedure) may use ultrasonic welding to attach the outer housing 205-*b* to the inner housing 205-*a* and form an arcuate frame for a ring 104. The welding process may involve ultrasonic welding, which may melt (e.g., bond, fuse) the one or more welding features to attach the outer housing to the inner housing and form the arcuate frame. Additionally, or alternatively, the welding process may include laser welding, heat welding, friction welding, radio frequency welding, or a combination thereof.

To reduce negative effects on fragile components, such as a PCB of the ring 104, the fragile components may be disposed in a location away from the welding features. It may be appreciated that the distance that the PCB components are moved from the welding features is dependent on the overall size of the wearable device and on the size of the PCB components, the sensitivity of the PCB components, the presence or absence of protective shielding features, among other considerations. It can be determined by persons of ordinary skill in the art based on these features (among others) just how far away the welding features should be placed from the sensitive PCB components to avoid damage to the PCB components during the welding procedure. In some cases, a material may be used to cover and shield the fragile components from ultrasonic waves during the welding operation. In some examples, one or more ultrasonic welding heads may be designed in a circular shape, allowing the entire ring 104 to be welded concurrently during the ultrasonic welding operation. In some examples, transparent lenses for the ring 104 may be added to the inner housing 205-*a* (e.g., as molded plastic) and integrated into the inner housing 205-*a*, which may allow the ring 104 to collect physiological data from a user 102 via one or more sensors (e.g., within the PPG system 235), as described herein.

Accordingly, by incorporating these techniques involving the welding features, rings 104 may be formed from plastic materials using a welding procedure while protecting fragile components of the rings 104, thereby reducing material costs and speeding up production relative to using metal materials.

Figure 3:
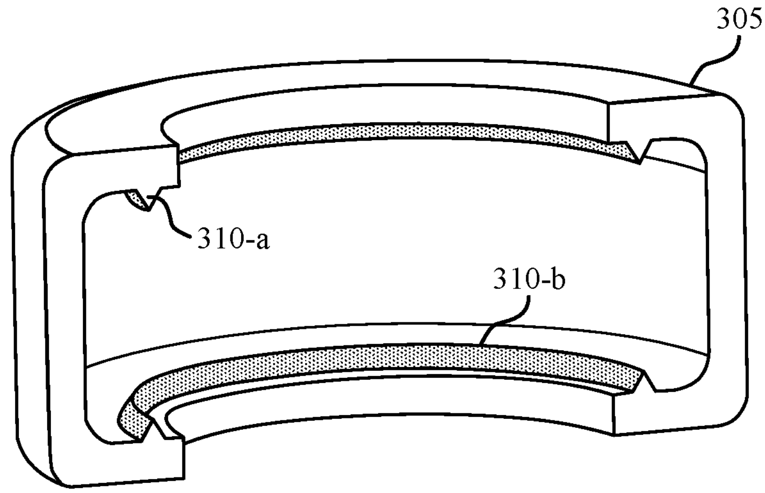
FIG. 3 shows an example of a diagram that supports low cost ring device structures in accordance with aspects of the present disclosure.
Figure 3:

FIG. 3 shows an example of a diagram 300 that supports low cost ring device structures in accordance with aspects of the present disclosure. The diagram 300 may illustrate a cross-sectional view bisecting an outer lateral surface cover 305, which may be an example of the outer housing 205-*b* described herein, with reference to FIG. 2.

The outer lateral surface cover 305 may include one or more welding features 310. For example, the outer lateral surface cover 305 may include a welding feature 310-*a* and a welding feature 310-*b*. In some examples, as shown, each welding feature may extend radially around a portion of the outer lateral surface cover 305. For instance, the welding feature 310-*a* may extend radially around a first portion (e.g., an upper portion) of the outer lateral surface cover 305, and the welding feature 310-*b* may extend radially around a second portion (e.g., a lower portion) of the outer lateral surface cover 305.

Figure 4:
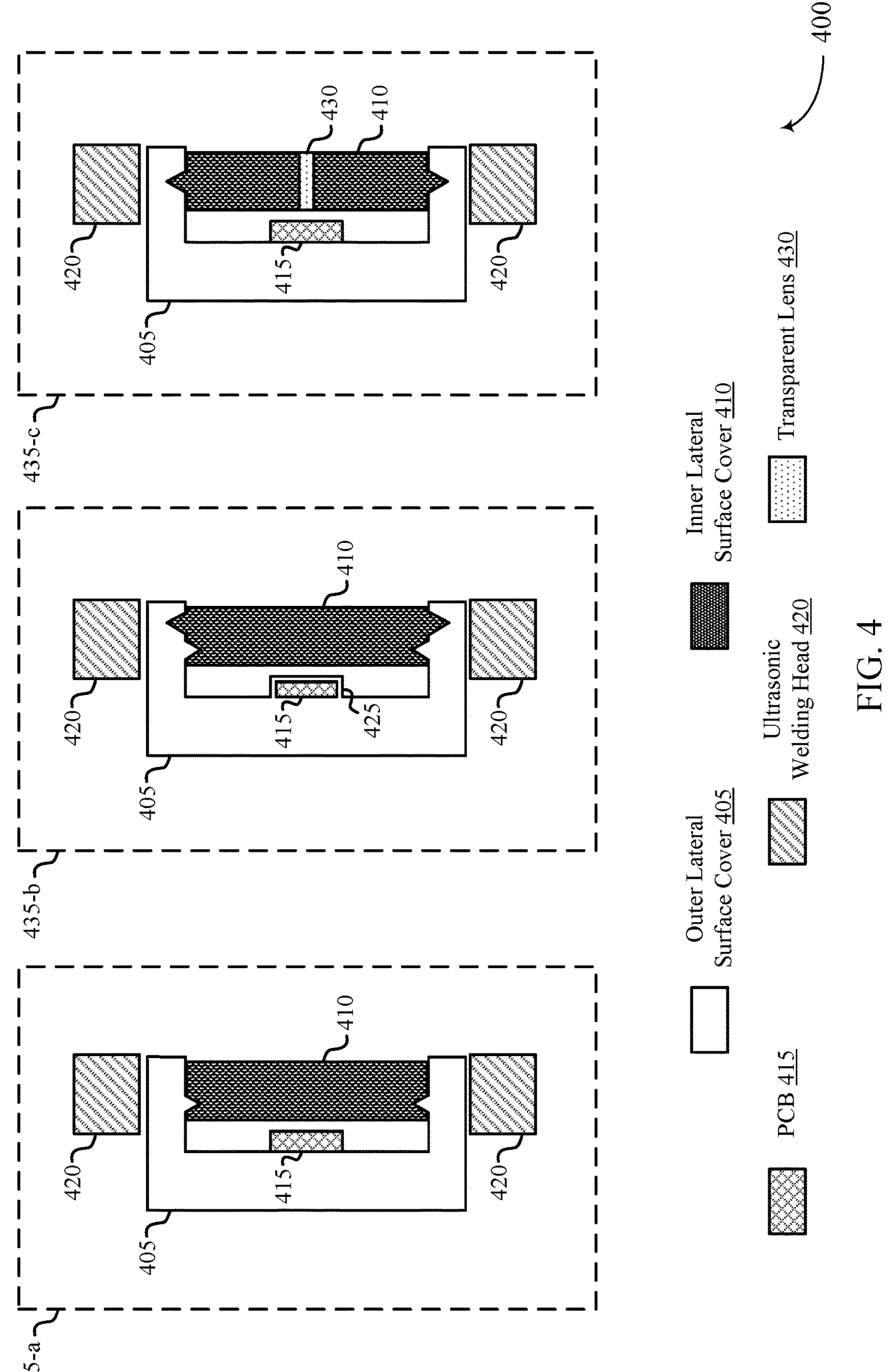
FIG. 4 shows an example of a welding assembly diagram that supports low cost ring device structures in accordance with aspects of the present disclosure.

In some examples, the outer lateral surface cover 305 may have at least two welding features 310. In other examples, the outer lateral surface cover 305 may have more than two welding features, which may help achieve a greater bond (e.g., weld) with an inner lateral surface cover based on an ultrasonic welding operation. For example, the outer lateral surface cover 305 may have two welding features 310 extending radially around the first portion (e.g., the upper portion), and the outer lateral surface cover 305 may have two welding features 310 extending radially around the second portion (e.g., the upper portion). Alternatively, the outer lateral surface cover 305 may have fewer welding features 310. For example, the outer lateral surface cover 305 may have no welding features 310 if the inner lateral surface cover includes one or more welding features 310 for welding to the outer lateral surface cover 305, as illustrated in FIG. 4.

The welding features 310 may have a triangular cross-sectional shape, as shown. This may facilitate melting of the welding features 310 during a welding procedure (e.g., an ultrasonic welding procedure) to weld the outer lateral surface cover 305 to an inner lateral surface cover, as the thinner portions may melt faster. In some other examples, however, different cross-sectional shapes may be used. For example, the welding features 310 may have rectangular cross-sectional shapes, which may have a width to allow them to melt during the welding procedure.

In some examples, the outer lateral surface cover 305 may be formed using injection molding techniques. For example, a molten plastic material, such as a polycarbonate material, may be deposited into a mold. The mold may include molds for welding features 310. As such, the plastic material may cool and solidify, forming the outer lateral surface cover 305 including the welding feature 310-*a* and the welding feature 310-*b*. In some examples, an inner lateral surface cover, as described herein, may also be formed using injection molding techniques.

Accordingly, by incorporating these techniques involving the welding features 310, wearable ring devices may be formed from plastic materials using a welding procedure while protecting fragile components of the wearable ring device, thereby reducing material costs, and speeding up production relative to using metal materials.

FIG. 4 shows an example of a welding assembly diagram 400 that supports low cost ring device structures in accordance with aspects of the present disclosure. The welding assembly diagram 400 may include an outer lateral surface cover 405 and an inner lateral surface cover 410, which may be examples of corresponding components as described herein, such as the outer housing 205-*b* and the inner housing 205-*a* described with reference to FIG. 2, or the outer lateral surface cover 305 described with reference to FIG. 3.

The welding assembly diagram 400 may illustrate different assemblies 435, such as an assembly 435-*a*, an assembly 435-*b*, and an assembly 435-*c* that may be used for forming a wearable ring device based on a welding procedure (e.g., an ultrasonic welding procedure), as described herein. Each assembly 435 may illustrate a cross-sectional view of various components.

The assembly 435-*a* illustrates an example where a first welding feature extends radially around a first portion of the outer lateral surface cover 405 and a second welding feature extends radially around a second portion of the outer lateral surface cover 405, as illustrated in FIG. 3. The welding features of the outer lateral surface cover 405 may intersect with the inner lateral surface cover 410, such that the welding features of the outer lateral surface cover 405 are welded to the inner lateral surface cover 410 via the welding procedure to form an arcuate frame for a wearable ring device.

The assembly 435-*a* may include ultrasonic welding heads 420 that may be used to perform the welding procedure. For example, the assembly 435-*a* may include a first ultrasonic welding head 420 above the outer lateral surface cover 405 and a second ultrasonic welding head 420 below the outer lateral surface cover 405. In some examples, the ultrasonic welding heads 420 may be or have a circular component. For example, the ultrasonic welding heads 420 may be circular, and may be in contact with a portion of the outer lateral surface cover 405 or the inner lateral surface cover 410 associated with (e.g., containing, adjacent with) the welding features during the welding procedure. Alternatively, the ultrasonic welding heads 420 may be ring-shaped, while still being in contact with the portion of the outer lateral surface cover 405 or the inner lateral surface cover 410 associated with the welding features during the welding procedure.

During the welding procedure, some pressure may be applied by the ultrasonic welding heads 420 such that an upper ultrasonic welding head 420 is in contact with an upper portion of the outer lateral surface cover 405 and a lower ultrasonic welding head is in contact with a lower portion of the outer lateral surface cover 405. The ultrasonic welding heads 420 may then vibrate at a high frequency (e.g., in a vertical direction), which may cause the welding features to heat up (e.g., due to friction). This may melt the welding features, which may flatten and cool after the ultrasonic welding heads 420 stop vibrating. As such, the outer lateral surface cover 405 may be welded to the inner lateral surface cover 410.

By using the two ultrasonic welding heads 420 each having a circular component in contact with the outer lateral surface cover 405 during the welding procedure, the upper portion of the outer lateral surface cover 405 and the lower portion of the outer lateral surface cover 405 may be concurrently welded to the inner lateral surface cover 410. In some examples, the lower ultrasonic welding head 420 may not be used, and instead a stationary fixture may be used. In these examples, however, the welding procedure may not be able to concurrently melt both welding features, and the welding procedure may be performed twice (e.g., after rotating the arcuate frame components).

In some examples, a PCB 415 may be disposed between the outer lateral surface cover 405 and the inner lateral surface cover 410. In some cases, the PCB 415 may be arcuate in shape, and may extend radially around an inner surface of the outer lateral surface cover 405. To protect the PCB 415 from the welding procedure, the PCB 415 may be located in a first section that is different from a second section in which the welding features are located and where the ultrasonic welding heads 420 meet with the outer lateral surface cover 405. In some examples, the first section may be located radially adjacent to the second section, towards the outer portion of the arcuate frame, while the second section may be located towards the inner portion of the arcuate frame. Additionally, or alternatively, the PCB 415 may be centered (e.g., in a vertical dimension) between an upper portion of the outer lateral surface cover 405 and a lower portion of the outer lateral surface cover 405, such that the PCB 415 is (e.g., about) a same distance from either welding feature. As such, the PCB 415 may be located away from the welding features during the welding procedure, which may reduce the heat that the PCB 415 may be exposed to, thereby shielding the PCB 415 during the welding procedure.

The assembly 435-*b* illustrates an example in which a third welding feature extends radially around a first portion of the inner lateral surface cover 410 and a fourth welding feature extends radially around a second portion of the inner lateral surface cover 410, in addition to the first and second welding features of the outer lateral surface cover 405. The welding features of the inner lateral surface cover 410 may intersect with the outer lateral surface cover 405, such that the welding features of the inner lateral surface cover 410 may be welded to the outer lateral surface cover 405 via the welding procedure to form the arcuate frame for the wearable ring device.

The assembly 435-*b* also illustrates the use of a shielding component 425. In some examples, the PCB 415 may be disposed within the shielding component 425 to shield the PCB 415 from the heat generated due to the welding procedure. For example, the shielding component 425 may hold the PCB 415 in the first section away from the second section associated with the welding features, the shielding component 425 may insulate the PCB 415 from the heat, or both. In some examples, the shielding component 425 may be part of the outer lateral surface cover 405, and may be formed (e.g., from a plastic material, such as polycarbonate) with the outer lateral surface cover 405 in an injection molding procedure. Alternatively, the shielding component 425 may be a different material, such as an insulating material.

The assembly 435-*c* illustrates an example in which the inner lateral surface cover 410 includes two welding features that extend radially around the inner lateral surface cover 410, and the outer lateral surface cover 405 does not include welding features. The welding features of the inner lateral surface cover 410 may intersect with the outer lateral surface cover 405, such that the welding features of the inner lateral surface cover 410 may be welded to the outer lateral surface cover 405 via the welding procedure to form the arcuate frame for the wearable ring device.

The assembly 435-*c* also illustrates including a transparent lens 430 within the inner lateral surface cover 410. While one transparent lens 430 is shown, the inner lateral surface cover 410 may include multiple transparent lenses 430. For example, the inner lateral surface cover 410 may include one transparent lens 430 for an optical receiver of a PPG system and two transparent lenses 430 for optical transmitters of the PPG system, as described herein with reference to FIG. 2. Alternatively, one larger transparent lens 430 may be used that may allow light to be transmitted and emitted from all components in the PPG system. Accordingly, the PCB 415 may perform measurements of physiological data of a user using one or more sensors via the one or more transparent lenses 430.

Accordingly, by incorporating these techniques involving the welding features, wearable ring devices may be formed from plastic materials using a welding procedure while protecting fragile components of the wearable ring device, thereby reducing material costs, and speeding up production relative to using metal materials.

Figure 5:
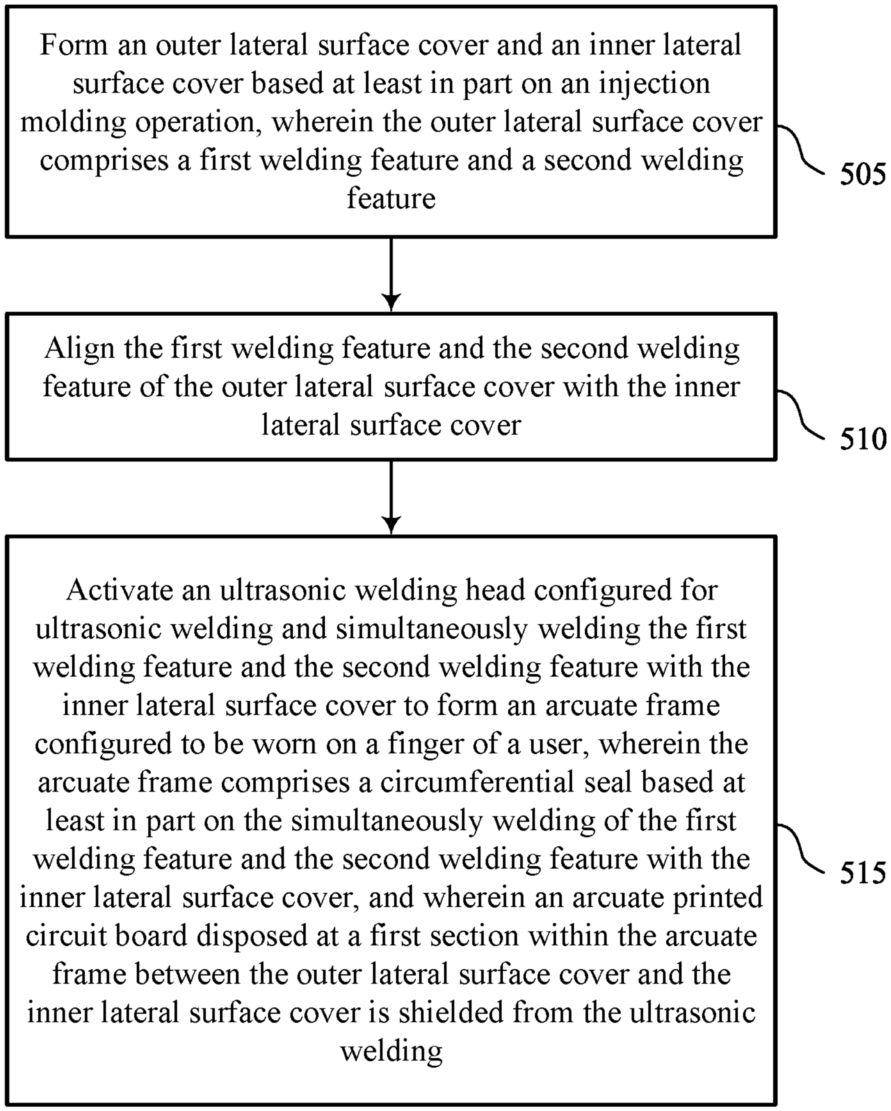
FIGS. 5 and 6 show flow charts illustrating methods that support low cost ring device structures in accordance with aspects of the present disclosure.

FIG. 5 shows a flowchart illustrating a method 500 that supports low cost ring device structures in accordance with aspects of the present disclosure. The operations of the method 500 may be implemented by a wearable device or its components as described herein. For example, the operations of the method 500 may be performed by a wearable device as described with reference to FIGS. 1 through 4. In some examples, a wearable device may execute a set of instructions to control the functional elements of the wearable device to perform the described functions. Additionally, or alternatively, the wearable device may perform aspects of the described functions using special-purpose hardware.

At 505, the method may include forming an outer lateral surface cover and an inner lateral surface cover based at least in part on an injection molding operation, wherein the outer lateral surface cover comprises a first welding feature and a second welding feature. The operations of block 505 may be performed in accordance with examples as disclosed herein.

At 510, the method may include aligning the first welding feature and the second welding feature of the outer lateral surface cover with the inner lateral surface cover. The operations of block 510 may be performed in accordance with examples as disclosed herein.

At 515, the method may include activating an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding. The operations of block 515 may be performed in accordance with examples as disclosed herein.

Figure 6:
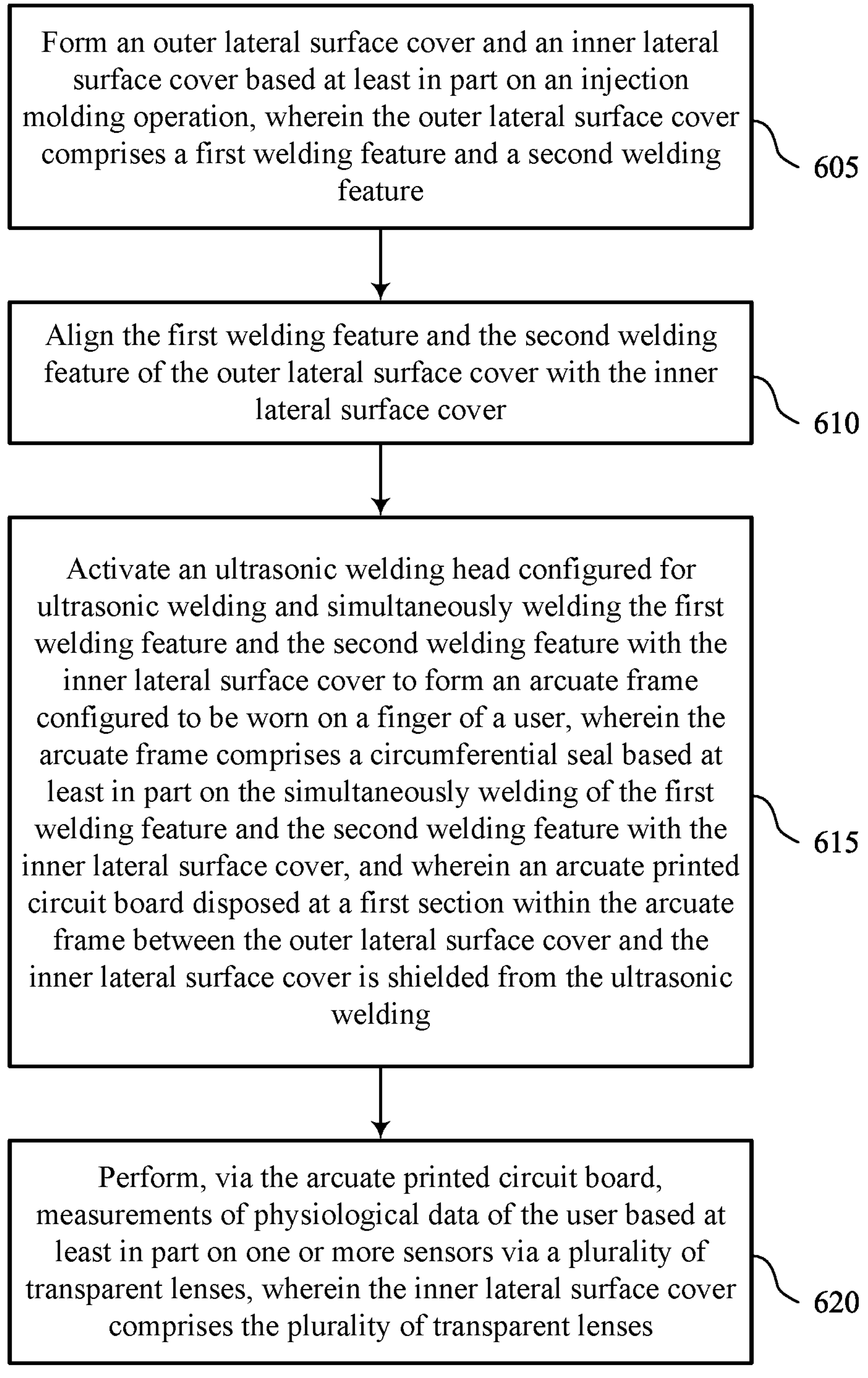

FIG. 6 shows a flowchart illustrating a method 600 that supports low cost ring device structures in accordance with aspects of the present disclosure. The operations of the method 600 may be implemented by a wearable device or its components as described herein. In some examples, a wearable device may execute a set of instructions to control the functional elements of the wearable device to perform the described functions. Additionally, or alternatively, the wearable device may perform aspects of the described functions using special-purpose hardware.

At 605, the method may include forming an outer lateral surface cover and an inner lateral surface cover based at least in part on an injection molding operation, wherein the outer lateral surface cover comprises a first welding feature and a second welding feature. The operations of block 605 may be performed in accordance with examples as disclosed herein.

At 610, the method may include aligning the first welding feature and the second welding feature of the outer lateral surface cover with the inner lateral surface cover. The operations of block 610 may be performed in accordance with examples as disclosed herein.

At 615, the method may include activating an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding. The operations of block 615 may be performed in accordance with examples as disclosed herein.

At 620, the method may include performing, via the arcuate printed circuit board, measurements of physiological data of the user based at least in part on one or more sensors via a plurality of transparent lenses, wherein the inner lateral surface cover comprises the plurality of transparent lenses. The operations of block 620 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

A method is described. The method may include forming an outer lateral surface cover and an inner lateral surface cover based at least in part on an injection molding operation, wherein the outer lateral surface cover comprises a first welding feature and a second welding feature, aligning the first welding feature and the second welding feature of the outer lateral surface cover with the inner lateral surface cover, and activating an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding.

An apparatus is described. The apparatus may include at least one processor, at least one memory coupled with the at least one processor, and instructions stored in the at least one memory. The instructions may be executable by the at least one processor to cause the apparatus to form an outer lateral surface cover and an inner lateral surface cover based at least in part on an injection molding operation, wherein the outer lateral surface cover comprises a first welding feature and a second welding feature, align the first welding feature and the second welding feature of the outer lateral surface cover with the inner lateral surface cover, and activate an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding.

Another apparatus is described. The apparatus may include means for forming an outer lateral surface cover and an inner lateral surface cover based at least in part on an injection molding operation, wherein the outer lateral surface cover comprises a first welding feature and a second welding feature, means for aligning the first welding feature and the second welding feature of the outer lateral surface cover with the inner lateral surface cover, and means for activating an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding.

A non-transitory computer-readable medium storing code is described. The code may include instructions executable by a processor to form an outer lateral surface cover and an inner lateral surface cover based at least in part on an injection molding operation, wherein the outer lateral surface cover comprises a first welding feature and a second welding feature, align the first welding feature and the second welding feature of the outer lateral surface cover with the inner lateral surface cover, and activate an ultrasonic welding head configured for ultrasonic welding and simultaneously welding the first welding feature and the second welding feature with the inner lateral surface cover to form an arcuate frame configured to be worn on a finger of a user, wherein the arcuate frame comprises a circumferential seal based at least in part on the simultaneously welding of the first welding feature and the second welding feature with the inner lateral surface cover, and wherein an arcuate printed circuit board disposed at a first section within the arcuate frame between the outer lateral surface cover and the inner lateral surface cover is shielded from the ultrasonic welding.

In some examples of the method, apparatuses, and non-transitory computer-readable medium described herein, the ultrasonic welding head comprises a first circular component and a second circular component, the first circular component being in contact with a first portion of the outer lateral surface cover during the ultrasonic welding, and the second circular component being in contact with a second portion of the outer lateral surface cover during the ultrasonic welding.

In some examples of the method, apparatuses, and non-transitory computer-readable medium described herein, the outer lateral surface cover comprises a shielding component and the arcuate printed circuit board may be disposed within the shielding component to shield the arcuate printed circuit board from the ultrasonic welding.

In some examples of the method, apparatuses, and non-transitory computer-readable medium described herein, the first welding feature and the second welding feature may be located in a second section different from the first section to shield the arcuate printed circuit board from the ultrasonic welding.

In some examples of the method, apparatuses, and non-transitory computer-readable medium described herein, the first welding feature extends radially around a first portion of the outer lateral surface cover and the second welding feature extends radially around a second portion of the outer lateral surface cover.

In some examples of the method, apparatuses, and non-transitory computer-readable medium described herein, the inner lateral surface cover comprises a third welding feature extending radially around a first portion of the inner lateral surface cover and a fourth welding feature extending radially around a second portion of the inner lateral surface cover.

In some examples of the method, apparatuses, and non-transitory computer-readable medium described herein, activating the ultrasonic welding head may include operations, features, means, or instructions for welding the third welding feature of the inner lateral surface cover to the first welding feature of the outer lateral surface cover to form the arcuate frame and welding the fourth welding feature of the inner lateral surface cover to the second welding feature of the outer lateral surface cover to form the arcuate frame.

Some examples of the method, apparatuses, and non-transitory computer-readable medium described herein may further include operations, features, means, or instructions for performing, via the arcuate printed circuit board, measurements of physiological data of the user based at least in part on one or more sensors via a plurality of transparent lenses, wherein the inner lateral surface cover comprises the plurality of transparent lenses.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device, comprising:

an arcuate frame configured to be worn on a finger of a user, the arcuate frame comprising:

an inner cover comprising an inner surface of the wearable ring device that is configured to contact the finger of the user when the wearable ring device is worn by the user; and an outer cover comprising an outer surface of the wearable ring device, wherein a first welding rib extends from a first portion of the outer cover of the arcuate frame, wherein a second welding rib extends from a second portion of the outer cover of the arcuate frame, wherein the first welding rib and the second welding rib extend from the outer cover towards one another within the wearable ring device, and wherein the first welding rib and the second welding rib are welded to the inner cover to form the arcuate frame; and an arcuate printed circuit board coupled with the outer cover and disposed within the arcuate frame between the outer cover and the inner cover.

2. The wearable ring device of claim 1, wherein the arcuate printed circuit board is disposed in a first section within the arcuate frame, and wherein the first welding rib and the second welding rib are located in a second section different from the first section, wherein the first section is closer than the second section to the outer surface of the wearable ring device in a dimension extending from the inner surface of the wearable ring device toward the outer surface of the wearable ring device.

3. The wearable ring device of claim 1, wherein the inner cover comprises a plurality of transparent lenses and the arcuate printed circuit board is configured to perform measurements of physiological data of the user based at least in part on one or more sensors via the plurality of transparent lenses.

4. The wearable ring device of claim 1, wherein the first welding rib and the second welding rib are at least partially deformed via an ultrasonic welding procedure to secure the inner cover with the outer cover.

5. The wearable ring device of claim 1, wherein the arcuate frame comprises a shielding component between the outer cover and the inner cover, and wherein the arcuate printed circuit board is disposed within the shielding component.

6. The wearable ring device of claim 5, wherein the shielding component is positioned between the arcuate printed circuit board and the first welding rib and the second welding rib.

7. The wearable ring device of claim 1, wherein:

a third welding feature extends around a first portion of the inner cover; and a fourth welding feature extends around a second portion of the inner cover, and wherein the third welding feature and the fourth welding feature are welded to the outer cover to form the arcuate frame.

8. The wearable ring device of claim 7, wherein the third welding feature is welded to the first welding rib, and wherein the fourth welding feature is welded to the second welding rib.

9. The wearable ring device of claim 1, wherein the outer cover further comprises a first side wall and a second side wall of the wearable ring device, wherein the first side wall comprises a first interior surface facing an interior of the wearable ring device, and wherein the second side wall comprises a second interior surface facing the interior of the wearable ring device, wherein the first welding rib extends from the first interior surface of the first side wall, and wherein the second welding rib extends from the second interior surface of the second side wall.

10. The wearable ring device of claim 9, wherein the first interior surface of the first side wall and the second interior surface of the second side wall are substantially parallel to one another, wherein the first welding rib extends from the first interior surface of the first side wall in a first direction that is substantially parallel to the outer surface of the wearable ring device, the inner surface of the wearable ring device, or both, and wherein the second welding rib extends from the second interior surface of the second side wall in a second direction that is substantially parallel to the outer surface of the wearable ring device, the inner surface of the wearable ring device, or both.

11. A wearable ring device, comprising:

an arcuate frame configured to be worn on a finger of a user, the arcuate frame comprising:

an inner cover comprising an inner surface of the wearable ring device that is configured to contact the finger of the user when the wearable ring device is worn by the user; and an outer cover comprising an outer surface of the wearable ring device, wherein a first welding rib extends from a first portion of the inner cover of the arcuate frame, wherein a second welding rib extends from a second portion of the inner cover of the arcuate frame, wherein the first welding rib and the second welding rib extend from the inner cover away from one another within the wearable ring device, and wherein the first welding rib and the second welding rib are welded to the outer cover to form the arcuate frame; and an arcuate printed circuit board coupled with the outer cover and disposed within the arcuate frame between the outer cover and the inner cover.

12. The wearable ring device of claim 11, wherein the arcuate printed circuit board is disposed in a first section within the arcuate frame, and wherein the first welding rib and the second welding rib are located in a second section different from the first section, wherein the first section is closer than the second section to the outer surface of the wearable ring device in a dimension extending from the inner surface of the wearable ring device toward the outer surface of the wearable ring device.

13. The wearable ring device of claim 11, wherein the inner cover comprises a plurality of transparent lenses, and wherein the arcuate printed circuit board is configured to perform measurements of physiological data of the user based at least in part on one or more sensors via the plurality of transparent lenses.

14. The wearable ring device of claim 11, wherein the first welding rib and the second welding rib are at least partially deformed via an ultrasonic welding procedure to secure the inner cover with the outer cover.

15. The wearable ring device of claim 11, wherein the arcuate frame comprises a shielding component between the outer cover and the inner cover, and wherein the arcuate printed circuit board is disposed within the shielding component.

16. The wearable ring device of claim 15, wherein the shielding component is positioned between the arcuate printed circuit board and the first welding rib and the second welding rib.

17. The wearable ring device of claim 11, wherein the outer cover further comprises a first side wall and a second side wall of the wearable ring device, wherein the first side wall comprises a first interior surface facing an interior of the wearable ring device, and wherein the second side wall comprises a second interior surface facing the interior of the wearable ring device, wherein the first welding rib is coupled with the first interior surface of the first side wall, and wherein the second welding rib is coupled with the second interior surface of the second side wall.

18. The wearable ring device of claim 17, wherein the first interior surface of the first side wall and the second interior surface of the second side wall are substantially parallel to one another, wherein the first welding rib extends from the inner cover in a first direction that is substantially perpendicular to the first interior surface of the first side wall, and wherein the second welding rib extends from the inner cover in a second direction that is substantially perpendicular to the second interior surface of the second side wall.

* * * * *